United States Patent [19]

Edgar

[11] Patent Number: 4,965,361

[45] Date of Patent: Oct. 23, 1990

[54] PREPARATION OF 4-SUBSTITUTED ARYL OLEFINS

[75] Inventor: Kevin J. Edgar, Kingsport, Tenn.

[73] Assignee: Eastman Kodak Company, Rochester, N.Y.

[21] Appl. No.: 315,674

[22] Filed: Feb. 27, 1989

[51] Int. Cl.⁵ ............... C07D 215/16; C07D 213/127; C07F 13/00

[52] U.S. Cl. .................................. 516/179; 546/261; 556/12; 568/737; 568/796; 570/182; 560/105; 562/496

[58] Field of Search ............... 546/179, 261; 568/737, 568/796; 570/182; 556/12; 562/496; 560/105

[56] References Cited

PUBLICATIONS

Ziegler & Heck, "Palladium-Catalyzed Vinylic Substitution with Highly Activated Aryl Halides," Journal of Organic Chemistry, vol. 43 (No. 15), pp. 2941-2946 (1978).

Plevyak & Heck, "Palladium-Catalyzed Arylation of Ethylene," Journal of Organic Chemistry, vol. 43 (No. 12), pp. 2454-2456 (1978).

Heck, "New Applications of Palladium in Organic Synthesis, " Pure & Applied Chemistry, vol. 50, pp. 691-701 (1978).

Heck, "Palladium-Catalyzed Reactions of Organic Halides with Olefins," Accounts of Chemical Research, vol. 12, pp. 146-151 (1979).

Heitz et al., "Synthesis of Monomers and Polymers by the Heck Reaction," Makromolecular Chem., vol. 189, pp. 119-127 (1988).

*Primary Examiner*—David B. Springer
*Attorney, Agent, or Firm*—J. Frederick Thomsen; William P. Heath; s. E. Reiter

[57] ABSTRACT

Process is disclosed for the preparation of 4-substituted aryl olefins from 4-substituted aryl iodides. 4-Substituted aryl iodides are contacted with an olefin in an ester solvent in the presence of a catalyst system comprising a palladium compound and a Bronsted base.

13 Claims, No Drawings

PREPARATION OF 4-SUBSTITUTED ARYL OLEFINS

DESCRIPTION

This invention relates to the preparation of 4-substituted aryl olefins. In one aspect, this invention relates to the preparation of 4-hydroxyaryl olefins. In another aspect, this invention relates to the preparation of 4-alkoxyaryl olefins. In yet another aspect, this invention relates to the preparation of 4-acyloxyaryl olefins. In a further aspect, this invention relates to reactions of 4-substituted aryl iodides.

BACKGROUND

Hydroxyaryl, alkoxyaryl and acyloxyaryl olefins are of considerable commercial interest. These compounds are useful, for example, as monomers for the preparation of vinyl polymers. These materials can be polymerized by cationic and radical polymerization techniques. In some cases, these compounds can also be polymerized by anionic polymerization techniques.

The resulting poly(hydroxystyrene) polymers are useful in a wide variety of applications, e.g., in photoresists, in epoxy resins, as metal coatings, and the like. It is clear, therefore, that economical methods for the production of these materials would be of great interest.

One method known in the art for the preparation of such materials is the palladium-catalyzed reaction of certain aryl halides with olefins (commonly referred to as the "Heck" reaction) to afford certain styrene derivatives. For example, R. F. Heck (*Pure and Applied Chemistry*, Volume 50, Pages 691–701 (1978)) discloses the reaction of certain aryl bromides and iodides with methyl acrylate and dimethyl fumarate to provide the corresponding cinnamic acid derivatives.

A common problem with the "Heck" reaction is the production of stilbene type by-products even when the most simple of olefins (i.e., ethylene) is employed. See, for example Plevyak and Heck in *Journal of Organic Chemistry*, Volume 43, Pages 2454–2456 (1978). One prior art means employed to improve product yields in the "Heck" reaction is the addition of certain phosphine ligands for the palladium catalyst. See, for example, Ziegler and Heck in *Journal of Organic Chemistry*, Volume 43, Pages 2941–2946 (1978). While the use of such ligands does provide for improved yields of the desired styrene-type products, such ligands are extremely expensive and, therefore, render such conversions relatively unattractive for commercial scale operation.

Solvents disclosed in the prior art as useful for the "Heck" reaction are typically highly polar, water-miscible solvents. Such materials render product recovery and recycle of catalyst materials extremely difficult. Consequently, the "Heck" reaction as known in the art suffers many limitations which render it undesirable to carry out the process on other than a laboratory scale.

Few examples exist in the literature of the "Heck" reaction being used for the production of 4-hydroxyaryl olefins or 4-acyloxyaryl olefins. Such examples as do exist suggest that only highly reactive olefins, e.g., styrene and methyl acrylate, are useful in such processes. Such disclosures suggest that less reactive olefins than styrene or methyl acrylate would not be suitable for use in the Heck reaction with such 4-substituted aryl halides.

There is, therefore, a need for a process of producing 4-substituted aryl olefins which employs inexpensive catalyst components, allows for easy product recovery and catalyst recycle, and is effective even with olefins of relatively low reactivity.

STATEMENT OF THE INVENTION

In accordance with the present invention, 4-substituted aryl olefins are prepared in high yield by contacting a 4-substituted aryl iodide with an olefin in an ester solvent in the presence of a catalyst system comprising a palladium compound and a Bronsted base.

The practice of the present invention allows for the production of a wide range of aryl olefins, with minimum formation of such undesirable by-products as stilbene and stilbene derivatives. Even olefins such as ethylene, which are not normally reactive in the Heck reaction, are amenable to the invention process. In addition, the invention process does not require the use of expensive phosphine ligands which are employed in some prior art processes.

DETAILED DESCRIPTION OF THE INVENTION

In accordance with the present invention, there is provided a method for the preparation of unsaturated 4-oxyaryl compounds of the structure:

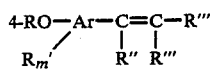

wherein R is selected from the group consisting of:
H,
$C_1$ up to $C_{20}$ alkyl or substituted alkyl moieties, acyl moieties of the structure:

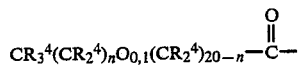

wherein each $R^4$ is independently selected from the group consisting of:
H,
alkyl and substituted alkyl moieties,
aryl and substituted aryl moieties,
halogens, and
wherein n is a whole number which falls in the range of 0 up to 20.
$R^5_3Si—$, wherein each $R^5$ is independently selected from alkyl moieties, substituted alkyl moieties, aryl moieties or substituted aryl moieties;
wherein each of R' and R''' are independently selected from
H,
$C_1$ up to $C_{20}$ alkyl or substituted alkyl,
$C_5$ up to $C_{14}$ aryl or substituted aryl,
acyl moieties of the structure:

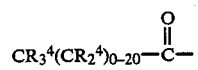

wherein each $R^4$ is selected independently from one another and are defined as set forth above, plus halides, a nitro group, and
sulfones or sulfoxides having the structure:

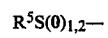

wherein $R^5$ is as defined above; wherein $R''$ is selected from the group consisting of:

H, and $C_1$ up to $C_5$ alkyl moieties;

wherein Ar is a $C_5$ up to $C_{14}$ hydrocarbyl- or heteroaromatic moiety; and wherein m can vary from 0 up to 4;

said method comprising contacting an aryl iodide of the formula:

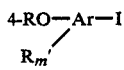

with a $C_2$ up to $C_{20}$ olefin or substituted olefin in the presence of a Bronsted base and a palladium catalyst under conditions suitable for the formation of the desired unsaturated aryl compound; wherein said contacting is carried out in the presence of an ester solvent of the structure:

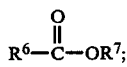

wherein each of $R^6$ and $R^7$ are selected independently from $C_1$ up to $C_5$ alkyl radicals, with the proviso that total number of carbon atoms contained by the $R^6$ plus the $R^7$ groups is no greater than 6.

Aryl iodides contemplated for use in the practice of the present invention are compounds of the formula

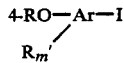

wherein Ar, R, R' and m are as defined above. Thus, a wide variety of substituted or unsubstituted 4-hydroxyaryl iodides, 4-alkoxyaryl iodides and 4-acyloxyaryl iodides are contemplated by the present invention. Preferred aromatic nuclei for the above structure include benzene, naphthalene, pyridine, and quinoline. The presently most preferred aromatic nuclei include phenyl, naphthyl or pyridyl moieties.

When m is greater than zero (i.e., one or more R' substituents are present) such substituents as alkyl groups, aryl groups, nitro groups, halogens and sulfone groups can be present. Presently preferred aryl iodides include 4-iodophenol, 4-iodophenyl acetate, t-butyl 4-iodophenyl carbonate, 4-iodo-2-methylphenol, 2-chloro-4-iodophenol, 2-bromo-4-iodophenol, 4-iodo-2-nitrophenol, 2-phenyl-4-iodophenol, 2-carboxy-4-iodophenol, 4-iodoanisole, 4-iodo-1-naphthol, 2-hydroxy-5-iodopyridine, 5-hydroxy-2-iodopyridine, 5-iodo-8-hydroxyquinoline, (4-iodophenoxy)trimethyl silane, or tert-butyl dimethyl 4-iodophenoxysilane.

Olefins contemplated for use in the practice of the present invention can vary widely. Typically, olefins having in the range of 2 up to 20 carbon atoms, and optionally substituted with a variety of substituents are contemplated. Typically, olefins employed in the practice of the present invention will conform to the structure:

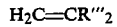

wherein $R'''$ is as defined above. Exemplary olefins include esters of acrylic acid, alkyl vinyl ketones, halogenated olefins, nitro olefins, vinyl alkyl sulfones, vinyl aryl sulfones, ethylene and its alkyl-substituted derivatives, and the like. Presently preferred olefins include ethylene, 1-octene, methyl acrylate, 1-buten-3-one, 1-nitroethylene, methyl vinyl sulfone or phenyl vinyl sulfone.

The palladium component of the catalyst system employed in the practice of the present invention can be provided to the reaction medium in any of a variety of forms. For example, palladium metal, palladium (II) compounds or palladium (0) complexes can be employed. Presently preferred source of palladium are palladium (II) compounds, because of the ready availability of such materials. Exemplary materials contemplated for use as the palladium component include palladium acetate, palladium chloride, tetrakis(triphenylphosphine)palladium, and the like.

The amount of palladium component employed in the practice of the present invention is not critical so long as sufficient quantity of palladium is present to catalyze the desired reaction. Preferably, the palladium component is present in a concentration in the range of about 0.02 mol percent up to about 20 mol percent, based on the moles of aryl iodide reactant. Preferably, in the range of about 0.1 up to 5 mol percent of palladium component is employed. As a result, the total reaction medium will typically have a palladium concentration in the range of about 4 up to 4,000 parts per million, with preferred palladium concentrations falling in the range of about 20 up to 1,000 parts per million.

Bronsted bases employed as a catalyst component in the practice of the present invention can vary widely. As employed herein, the term "Bronsted base" refers to any compound which can act as a proton acceptor in the reaction medium. Broadly, such materials as tertiary amines or compounds of the formula MY, wherein M is selected from the group consisting of alkali metals, alkaline earth metals, iron, manganese, zinc, and tin, and wherein Y is selected from the group consisting of hydroxide, formate, acetate, carbonate, carboxylate and alkoxide can be employed. Exemplary Bronsted bases include alkali metal carbonates, e.g., lithium carbonate, alkali metal acetates, e.g., lithium acetate, sodium acetate, potassium acetate, and the like; alkaline earth metal acetates, such as magnesium acetate, transition and non-transition metal acetates, e.g., iron acetate, manganese acetate, zinc acetate, tin acetate, and the like; pyridines, trialkylamines, e.g., triethylamine, tributylamine, trimethylamine; as well as mixtures of any two or more thereof. Presently preferred Bronsted bases for use in the practice of the present invention include triethylamine, sodium acetate, pyridine, sodium bicarbonate, and the like.

Ester solvents contemplated for use in the practice of the present invention are compounds having the structure

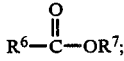

wherein each $R^6$ and $R^7$ are selected independently from $C_1$ up to $C_5$ alkyl radicals, with the proviso that total number of carbon atoms contained by the $R^6$ plus the $R^7$ groups is no greater than 6. Presently preferred ester solvents include methyl acetate and ethyl acetate, with methyl acetate being the presently most preferred solvent because excellent product yields are obtained with such solvent, product is readily recovered therefrom by well-known techniques. Catalyst recovery and recycle is also readily accomplished when the invention reaction is carried out in such solvent.

Conditions suitable for the formation of the desired unsaturated aryl compounds of the present invention can vary widely. For example, reaction temperature can vary in the range of about 75° up to 250° C., with temperatures in the range of about 100° up to 225° C. being preferred. The presently most preferred temperature range for the practice of the present invention falls in the range of about 100° up to 200° C. Substantially complete conversions are achieved at such reaction temperatures, thereby allowing for complete recycle of the expensive iodide moiety.

Those of skill in the art readily recognize that reaction pressures and reaction temperatures employed are interdependent, and thus can vary considerably. While the invention process can be carried out at pressures as high as 10,000 psig, reactions at such high pressure typically incur substantial utility and equipment costs such that commercial scale operation is not justified. Therefore, pressures in the range of about 10 up to 4,000 psig are presently preferred, with pressures in the range of about 100 up to 1,500 psig being the presently most preferred pressure range to employ. In the particular situation where a gaseous olefin is employed (e.g., ethylene), the reaction pressure employed will be at least high enough to maintain substantial quantities of the gaseous olefin in contact with the catalyst system and aryl iodide reactant so as to promote formation of the desired styrene derivative.

Contact times employed for the practice of the present invention can vary widely. Typically, contact times in the range of about 1 up to 20 hours are suitable for the formation of the desired styrene derivatives in good yields. Preferred contact times fall in the range of about 1 up to 10 hours.

The invention will now be described in greater detail by reference to the following non-limiting examples.

EXAMPLES

In the following examples, the materials employed were loaded into a 250 mL glass liner equipped with a magnetic stir bar. The liner was loaded into a steel autoclave designed to operate in a magnetically stirred mode, and the autoclave was sealed. When ethylene was the olefin used, the contents of the autoclave were heated to 50° C. with stirring. The autoclave was pressurized with the indicated amount of ethylene gas, then the contents were heated to the reaction temperature. The reaction mixture was stirred under ethylene pressure for the indicated reaction time, then the autoclave was cooled to 20° to 40° C. by a stream of cold air. After the gas was vented from the autoclave, the catalyst was recovered by filtration or decantation. The hydroiodide salt of the Bronsted base was removed by aqueous extraction of the reaction mixture. The sodium iodide may be recovered from the hydroiodide salt by neutralization. In some cases (volatile or crystalline amines) the Bronsted base may also be recovered and recycled. The desired aryl olefin was recovered from the organic layer by standard crystallization or distillation techniques, familiar to those of skill in the art. The results in the examples are from analysis of the crude organic products by gas chromatographic methods. The results of these runs are shown below.

EXAMPLE 1

Reagents set forth below were subjected to the standard procedure described above under the indicated reaction conditions. The results, in terms of yield of the desired 4-substituted aryl olefin and identification of other observed products, are also set forth below.

| Oxyiodoarene | 4-Iodophenol |
|---|---|
| Weight (g) | 2.00 |
| Catalyst | Palladium Acetate |
| Weight (g) | 0.046 |
| Base | Triethylamine |
| Weight (g) | 2.62 |
| Olefin | Ethylene |
| Pressure (Psig) | 1000 |
| Solvent | Methyl Acetate |
| Volume (mL) | 100 |
| Temperature (°C.) | 156 |
| Time (h) | 3 |
| % Yield | 90.3 |
| Products (mmoles) | Phenol (0.6) |
| | 4-Vinylphenol (21.3) |
| | 4-(1-Methoxyethyl)phenol (0.2) |
| | 4-Iodophenol (0.1) |

This example demonstrates the efficiency and selectivity of the invention method for the reaction of a 4-hydroxyaryl iodide with the unactivated olefin ethylene.

EXAMPLE 2

Reagents set forth below were subjected to the standard procedure described above under the indicated reaction conditions. The results, in terms of yield of the desired 4-substituted aryl olefin and identification of other observed products, are also set forth below.

| Oxyiodoarene | 4-Acetoxyiodobenzene |
|---|---|
| Weight (g) | 2.00 |
| Catalyst | Palladium Acetate |
| Weight (g) | 0.04 |
| Base | Triethylamine |
| Weight (g) | 0.85 |
| Olefin | Ethylene |
| Pressure (psig) | 1000 |
| Solvent | Methyl Acetate |
| Volume (mL) | 100 |
| Temperature (°C.) | 175 |
| Time (h) | 5 |
| Yield (%) | 86.0 |
| Products (mmoles) | Phenol (0.02) |
| | 4-Vinylphenol (0.47) |
| | 4-Vinylphenyl Acetate (6.56) |
| | 4-Iodophenol (0.03) |
| | 4-Iodophenyl Acetate (0.29) |

This example demonstrates the efficiency and selectivity of the invention method using a 4-acyloxyaryl iodide reactant.

EXAMPLE 3

Reagents set forth below were subjected to the standard procedure described above under the indicated reaction conditions. The results, in terms of yield of the desired 4-substituted aryl olefin and identification of other observed products, are also set forth below.

| Oxyiodoarene | 4-Iodophenol |
|---|---|
| Weight (g) | 2.00 |
| Catalyst | Palladium Acetate |
| Weight (g) | 0.02 |

|   |   |
|---|---|
| Base | Triethylamine |
| Weight (g) | 1.01 |
| Olefin | Methyl Acrylate |
| Weight (g) | 4.78 |
| Solvent | Methyl Acetate |
| Volume (mL) | 100 |
| Temperature (°C.) | 150 |
| Time (h) | 3 |
| Yield (%) | 79 |
| Products (mmoles) | Phenol (0.14) |
|   | 4-Iodophenol (0.59) |
|   | Methyl 4-Hydroxycinnamate (7.22) |

This example illustrates the efficiency and selectivity of the invention method employed an olefin reactant containing an electron-withdrawing group (methyl acrylate).

EXAMPLE 4

Reagents set forth below were subjected to the standard procedure described above under the indicated reaction conditions. The results, in terms of yield of the desired 4-substituted aryl olefin and identification of other observed products, and also set forth below.

|   |   |
|---|---|
| Oxyiodoarene | 4-Iodophenol |
| Weight (g) | 2.50 |
| Catalyst | Palladium Acetate |
| Weight (g) | 0.03 |
| Base | Triethylamine |
| Weight (g) | 1.26 |
| Olefin | Ethylene |
| Pressure (psig) | 1000 |
| Solvent | Ethyl Acetate |
| Volume (mL) | 100 |
| Temperature (°C.) | 150 |
| Time (h) | 3 |
| Yield (%) | 71.5 |
| Products (mmoles) | Phenol (0.46) |
|   | 4-Vinylphenol (8.12) |
|   | 4-Iodophenol (2.95) |

This example illustrates the less desirable product yields and lower level of aryl iodide conversion obtained when ester solvents other than the presently preferred methyl acetate are used in the practice of the present invention.

EXAMPLE 5

Reagents set forth below were subjected to the standard procedure described above under the indicated reaction conditions. The results, in terms of yield of the desired 4-substituted aryl olefin and identification of other observed products, are also set forth below.

|   |   |
|---|---|
| Oxyiodoarene | 4-Iodophenol |
| Weight (g) | 2.50 |
| Catalyst | Palladium Acetate |
| Weight (g) | 0.03 |
| Base | Triethylamine |
| Weight (g) | 1.26 |
| Olefin | Ethylene |
| Pressure (psig) | 500 |
| Solvent | Toluene |
| Volume (mL) | 100 |
| Temperature (°C.) | 150 |
| Time (h) | 3 |
| Yield (%) | 18.0 |
| Products (mmoles) | Phenol (0.32) |
|   | 4-Vinylphenol (2.04) |
|   | 4-Iodophenol (0.81) |

This example illustrates the extremely low yields of the desired aryl olefin obtained when aromatic hydrocarbon solvents are used rather than ester solvents in the practice of the present invention.

EXAMPLE 6

Reagents set forth below were subjected to the standard procedure described above under the indicated reaction conditions. The results, in terms of yield of the desired 4-substituted aryl olefin and identification of other observed products, are also set forth below.

|   |   |
|---|---|
| Oxyiodoarene | 4-Iodophenol |
| Weight (g) | 2.50 |
| Catalyst | Palladium Acetate |
| Weight (g) | 0.03 |
| Base | Triethylamine |
| Weight (g) | 1.26 |
| Olefin | Ethylene |
| Pressure (psig) | 500 |
| Solvent | Methanol |
| Volume (mL) | 100 |
| Temperature (°C.) | 150 |
| Time (h) | 3 |
| Yield (%) | 12.6 |
| Products (mmoles) | Phenol (0.09) |
|   | 4-Vinylphenol (1.43) |
|   | 4-(1-Methoxyethyl)phenol (6.16) |
|   | 4-Iodophenol (0.64) |

This example illustrates the fact that alcohols are not suitable solvents for the practice of the present invention, in part because they react further with the desired products to form saturated alkoxy adducts.

The invention has been described in detail with particular reference to preferred embodiments thereof, but it will be understood that variations and modifications can be effected within the spirit and scope of the invention.

I claim:

1. In a method for the preparation of unsaturated 4-oxyaryl compounds of the structure:

$$4\text{-RO}-\underset{R_m'}{Ar}-\underset{R''}{C}=\underset{R'''}{C}-R'''$$

wherein R is selected from the group consisting of:
H,
$C_1$ up to $C_{20}$ alkyl or substituted alkyl moieties, acyl moieties of the structure:

$$CR_3^4(CR_2^4)_nO_{0,1}(CR_2^4)_{20-n}-\overset{O}{\overset{\|}{C}}-$$

wherein each $R^4$ is independently selected from the group consisting of:
H,
alkyl and substituted alkyl moieties,
aryl and substituted aryl moieties,
halogens, and
wherein n is a whole number which falls in the range of 0 up to 20;
$R^5_3Si-$, wherein each $R^5$ is independently selected from alkyl moieties, substituted alkyl moieties, aryl moieties or substituted aryl moieties;
wherein each of R' and R''' are independently selected from
H, $C_1$ up to $C_{20}$ alkyl or substituted alkyl,
$C_5$ up to $C_{14}$ aryl or substituted aryl,
acyl moieties of the structure:

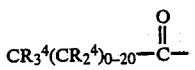

wherein each $R^4$ is selected independently from one another and are defined as set forth above, halides, a nitro group, and
sulfones or sulfoxides having the structure:

wherein $R^5$ is as defined above;
wherein R" is selected from the group consisting of:
H,
$C_1$ up to $C_5$ alkyl moieties;
wherein Ar is a $C_5$ up to $C_{14}$ hydrocarbyl- or hetero-aromatic moiety; and
wherein m can vary from 0 up to 4;
said method comprising contacting an aryl iodide of the formula:

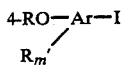

with a $C_2$ up to $C_{20}$ olefin or substituted olefin in the presence of a Bronsted base and a palladium catalyst under conditions suitable for the formation of the desired unsaturated aryl compound; the improvement wherein said contacting is carried out in the presence of an ester solvent of the structure:

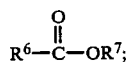

wherein each of $R^6$ and $R^7$ are selected independently from $C_1$ up to $C_5$ alkyl radicals, with the proviso that total number of carbon atoms contained by the $R^6$ plus the $R^7$ groups is no greater than 6.

2. A method is accordance with claim 1 wherein said solvent is selected from methyl acetate or ethyl acetate.

3. A method in accordance with claim 1 wherein said solvent is methyl acetate.

4. A method in accordance with claim 1 wherein R is H, methyl, trimethyl silyl or acetyl, x is 0 and Ar is phenyl, naphthyl or pyridyl.

5. A method in accordance with claim 1 wherein said aryl iodide is selected from 4-iodophenol, 4-iodophenyl acetate, t-butyl 4-iodophenyl carbonate, 4-iodo-2-methylphenol, 2-chloro-4-iodophenol, 2-bromo-4-iodophenol, 4-iodo-2-nitrophenol, 2-phenyl-4-iodophenol, 2-carboxy-4-iodophenol, 4-iodoanisole, 4-iodo-1-naphthol, 2-hydroxy-5-iodopyridine, 5-hydroxy-2-iodopyridine, 5-iodo-8-hydroxyquinoline, (4-iodophenoxy)-trimethyl silane, or tert-butyl dimethyl 4-iodophenoxysilane.

6. A method in accordance with claim 1 wherein said olefin has the structure:

wherein R''' is as defined above.

7. A method in accordance with claim 1 wherein said olefin is selected from ethylene, 1-octene, methyl acrylate, 1-buten-3-one, 1-nitroethylene, methyl vinyl sulfone or phenyl vinyl sulfone.

8. A method in accordance with claim 1 wherein said Bronsted base is selected from tertiary amines, or compounds of the formula MY, wherein M is selected from the group consisting of alkali metals, alkaline earth metals, iron, manganese, zinc, and tin; and wherein Y is selected from the group consisting of hydroxide, formate, acetate, carbonate, carboxylate and alkoxide.

9. A method in accordance with claim 1 wherein said Bronsted base is triethylamine, sodium acetate or pyridine.

10. A method in accordance with claim 1 wherein said palladium catalyst is provided in the form of elemental palladium, a palladium (II) compound or a palladium (0) complex.

11. A method in accordance with claim 10 wherein said palladium catalyst is a palladium (II) compound.

12. A method in accordance with claim 11 wherein said palladium (II) compound is palladium acetate.

13. A method in accordance with claim 1 wherein said conditions suitable for the formation of the desired unsaturated aryl compound comprise a reaction temperature in the range of about 75 up to 250 degrees C., at a pressure in the range of about atmospheric up to 10,000 psig, for a time in the range of about 1 up to 20 hours.

* * * * *